(12) United States Patent
McKenzie et al.

(10) Patent No.: US 6,518,307 B2
(45) Date of Patent: Feb. 11, 2003

(54) CONTROL OF MICROBIAL POPULATIONS IN THE GASTROINTESTINAL TRACT OF ANIMALS

(75) Inventors: K. Scott McKenzie, Bryan, TX (US); Anthony Giletto, College Station, TX (US); G. Duncan Hitchens, Bryan, TX (US); Billy M. Hargis, Fayetteville, AR (US); Kelly L. Herron, Houston, TX (US)

(73) Assignees: Lynntech, Inc., College Station, TX (US); The Texas A&M University System, College Station, TX (US)

( * ) Notice: Subject to any disclaimer, the term of this patent is extended or adjusted under 35 U.S.C. 154(b) by 0 days.

(21) Appl. No.: 09/981,669

(22) Filed: Oct. 17, 2001

(65) Prior Publication Data

US 2002/0115719 A1 Aug. 22, 2002

Related U.S. Application Data

(63) Continuation of application No. 09/487,966, filed on Jan. 18, 2000, now Pat. No. 6,342,528.

(51) Int. Cl.[7] .............................................. A01N 37/00
(52) U.S. Cl. ...................... 514/557; 514/574; 514/578; 424/405
(58) Field of Search ................................ 514/557, 574, 514/578; 424/405

(56) References Cited

U.S. PATENT DOCUMENTS

| | | |
|---|---|---|
| 4,320,116 A | 3/1982 | Bjorck |
| 4,726,948 A | 2/1988 | Prieels et al. |
| 5,110,583 A | 5/1992 | Sampathkumar |
| 5,122,538 A | 6/1992 | Lokkesmoe |
| 5,364,879 A | 11/1994 | Herman |
| 5,674,538 A | 10/1997 | Lokkesmoe et al. |
| 5,718,910 A | 2/1998 | Oakes et al. |
| 5,785,867 A | 7/1998 | LaZomby et al. |
| 5,849,289 A | 12/1998 | Dobrogosz et al. |
| 6,010,729 A | 1/2000 | Gutzmann et al. |
| 6,165,483 A | 12/2000 | Hel et al. |

FOREIGN PATENT DOCUMENTS

| | | |
|---|---|---|
| EP | 0233731 | 8/1987 |
| WO | WO 91/08981 | 6/1991 |
| WO | WO 97/26908 | 7/1997 |
| WO | WO 01/52827 A1 | 7/2001 |

OTHER PUBLICATIONS

Evaluation of Potential Disinfectants for Preslaught Broiler Crop Decontamination, E. T. Barnhart, L. L. Sarlin, D. J. Caldwell, J. A. Byrd, D. E. Corrier, B. M. Hargis, Jan. 30, 1998.

*Primary Examiner*—James H. Reamer
(74) *Attorney, Agent, or Firm*—Streets & Streets; Jeffrey L. Streets

(57) ABSTRACT

The present invention provides a method for controlling microbial populations in the gastrointestinal tract of animals. The method comprises the step of orally administering an effective amount of a peracid to an animal. Percarboxylic acids useful in this invention include peracetic acid, perpropionic acid, perbutyric acid, peroctanoic acid, perglycolic acid, perglutaric acid, persuccinic acid, perlactic acid, percitric acid, perdecanoic acid or mixtures thereof. These percarboxylic acids have been found to provide good antimicrobial action with good stability in aqueous streams. In addition to peracetic, peroctanoic and perdecanoic, particularly preferred percarboxylic acids include perpropionic, perbutyric, perglycolic, perlactic and percitric acids.

62 Claims, 3 Drawing Sheets

CONTROL OF MICROBIAL POPULATIONS IN THE GASTROINTESTINAL TRACT OF ANIMALS

This application is a continuation of application Ser. No. 09/487,966, filed Jun. 18, 2000, now U.S. Pat. No. 6,342,528.

This invention was made with government support under grant 99-33610-7433 awarded by the United States Department of Agriculture (USDA). The Government has certain rights in this invention.

BACKGROUND OF THE INVENTION

1. Field of the Invention

The present invention is related to methods for reducing and/or preventing microbial contamination in the gastrointestinal tract of animals.

2. Background of the Related Art

The Public Health Service/Centers for Disease Control and Prevention report that each year millions of Americans suffer illness caused by foodborne infection. The Centers for Disease Control and Prevention reported that 79% of outbreaks between 1987 and 1992 were bacterial. More recent data obtained through the CDC-FoodNet indicated that this trend has increased in 1998 to an alarming 94%, or 9,213 out of 9,787 confirmed cases of food derived infection. The reasons for these increases are not clear, though some microbes have demonstrated resistance to standard methods of preparation and storage of foods, not to mention a growing resistance to conventional antibiotics and disinfectants. Additional adverse pressures on the microbial character of fresh and processed foods include changes in agronomic and food processing practices, increased susceptibility of humans to certain pathogens, and the emergence of new virulent strains of bacterial, viral and emerging non-bacterial pathogens. The United States Department of Agriculture estimates that medical costs and productivity losses for 7 specific widespread pathogens in food range between $6.5 billion and $34.9 billion annually. These estimates do not include the total burden placed on society by the chronic illness caused by some foodborne pathogens.

Research in the meat industry has clearly shown that a principle source of pathogen contamination on animal carcasses is the contents of the gastrointestinal (GI) tract (ingesta). Due to the methods and equipment used during the processing of meat animals and poultry, it is impossible to prevent tearing of various constituents of the GI tract and subsequently releasing all or portions of the ingesta onto the fresh meat surfaces. The prevalence of Salmonella and Campylobacter on retail poultry carcasses remains a significant public health concern. Salmonella and Campylobacter together are thought to be responsible for the majority of acute cases of gastroenteritis. *E. coli* O157:H7 was first recognized as a human pathogen in 1982 when two outbreaks in the United States were associated with consumption of undercooked hamburgers from a fast-food restaurant chain. The pathogen has since emerged as a major cause of bloody and nonbloody diarrhea, causing as many as 20,000 cases of gastroenteritis and 250 deaths per year in the United States. *Listeria monocytogenes* transmission has been recognized as a major source of human listeriosis since the early 1980s. Listeriosis can cause stillbirths, miscarriages, meningitis, or sepsis in immunocompromised hosts. Case-fatality rates as high as 40% have been reported during outbreaks. Outbreaks have been associated with ready-to-eat foods, including those produced from fresh-processed foods containing meat or animal derived ingredients. This serious food safety problem has led to the development of numerous technologies to address the spreading of animal ingesta onto the meat surfaces during slaughter or the disinfection of the ingesta prior to slaughter.

Current practices in confined animal production include placing the animals through a feed withdrawal period for 4 to 18 hours prior to transportation to the slaughter facility. It is during this feed withdrawal period that poultry begin to peck at the bedding material that, by the time the birds are ready to be shipped to the abattoir, becomes severely contaminated with feces. If these feces contain pathogenic bacteria (i.e., Salmonella or Campylobacter), these organisms will quickly colonize organ lumen areas throughout the digestive tract of the birds, especially in the upper GI tract.

Investigations of poultry processing plants have revealed that the primary digestive organ responsible for harboring most of the harmful upper GI tract bacteria is the crop. During automated evisceration procedures, the contents of the crop are almost always emptied onto processing equipment and/or onto the freshly exposed surface of the bird.

While colonization of the food animal's gastrointestinal tract may or may not cause disease in the animal itself, removal of GI tract bacterial does decrease the foodborne disease risk associated with consumption of meat and meat byproducts. However, recent data has suggested that colonization of the human GI tract by certain microbes may also lead to significant disease risk. It is estimated that 10% of the people of the US are afflicted by peptic ulcer disease. It is now generally accepted that a significant percentage of peptic ulcers in humans are caused by, or exacerbated by, one or more species of bacteria, including *Helicobacter pylori*. Additionally, other GI tract diseases thought to be linked to bacteria overpopulation include bowel inflamatory disease and sluggish bowel syndrome.

Therefore, there is a need for a method of controlling the microbial population in the gastrointestinal tract of animals. It would be desirable if the method involved non-invasive, oral administration of a biocidal compound or composition that could be added to drinking water, feed/foodstuffs, or other ingestible forms. It would be even more desirable if the presence of the compound or composition in water or feed/foodstuffs did not effect the consumption of the water or feed/foodstuffs by the animals. It would also be desirable if the compound or composition would decompose or form by-products that are harmless to the animal and, in the case of animals to be slaughtered for consumption, either the byproducts are not partitioned in or on the edible portions of the carcass or are harmless to those consuming the meat of the animal.

SUMMARY OF THE INVENTION

The invention is a process for preventing microbial growth in the digestive tract of living vertebrate animals, particularly food animals. Control of microbial growth is achieved by the step of applying a percarboxylic acid or a mixture of percarboxylic acids to an aqueous stream which is subsequently consumed orally by the animal. The formulation can also be mixed into food items or into particulate or similar materials, or packaged in ingestible capsules, whereby the active ingredient enters the body of the animal through the oral cavity through feeding behavior, or food scavenging, or particulate scavenging activities of the animal. Formulations may also be sprayed onto the outside of the animal and taken orally.

The process of the invention is unexpectedly effective in preventing the growth of unwanted microorganisms within body cavities and digestive tract of animals prior to the slaughter of the animal. The formulation exerts its decontaminating effect beyond the oral cavity and into the intestinal regions of the animal. The oral consumption of appropriately formulated percarboxylic acids causes an unexpectedly high level of internal decontamination of the animal.

The process of the invention provides an antimicrobial agent useful in poultry production, such as during the feed withdrawal period that usually extends 0.1 to 1.5 days prior to slaughter. A high degree of internal antimicrobial efficacy is combined with a high degree of palatability by the animal. The formulation can be safely ingested by animals or by humans while imposing no environmental incompatibility or ill health. The consumed percarboxylic formulations break down inside the animals body to harmless end products.

Differentiation of antimicrobial "-cidal" or "-static" activity, the definitions which describe the degree of efficacy, and the official laboratory protocols for measuring this efficacy are important considerations for understanding the relevance of antimicrobial agents and compositions. Antimicrobial compositions may effect two kinds of microbial cell damage. The first is a truly lethal, irreversible action resulting in complete microbial cell destruction or incapacitation. The second type of cell damage is reversible, such that if the organism is rendered free of the agent, it can again multiply. The former is termed bacteriocidal and the later, bacteriostatic. A sanitizer and a disinfectant are, by definition, agents which provide antibacterial or bacteriocidal activity. In contrast, a preservative is generally described as an inhibitor or bacteriostatic composition.

DETAILED DESCRIPTION

Figure 1:
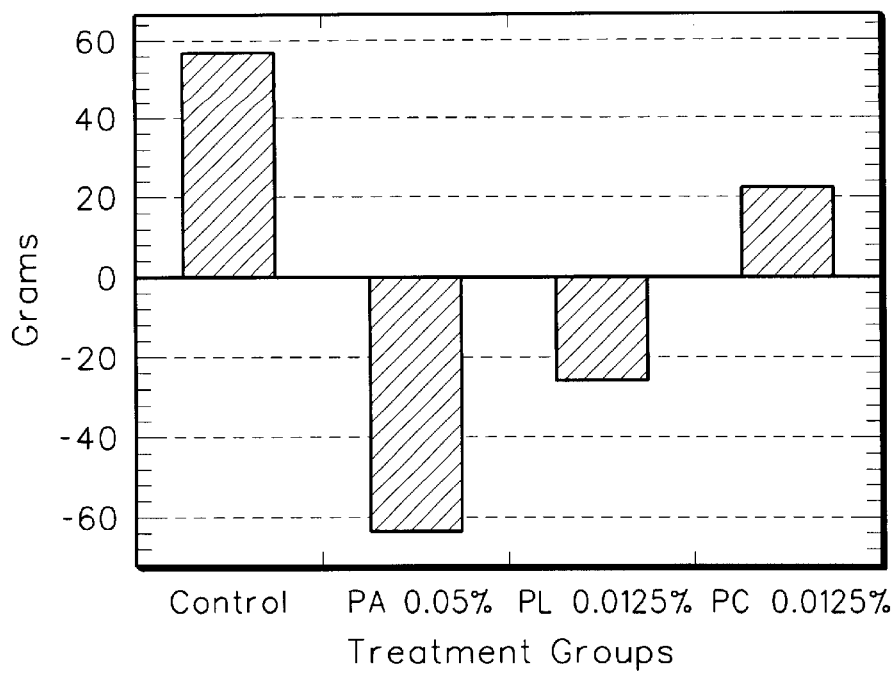
FIG. 1 is a graphical depiction of the mean weight loss or gain (grams) of broilers (n=20 per group) after 2 h exposure to peracetic acid (PA), perlactic acid (PL), or percitric acid (PC) in drinking water.

The present invention provides a method for controlling microbial populations in the gastrointestinal tract of animals. The method comprises the step of orally administering an effective amount of a peracid to an animal.

The term "animals" as used herein means humans and other vertebrate animals, including poultry, fish, cattle, swine, goats, lambs, dogs, cats, rodents, rabbits, birds, deer, non-human primates, and others.

If the peracid is to be delivered to a food animal for the purpose of preventing contamination of meat surfaces during slaughter, then it is preferred that the peracid is administered over a period just preceding slaughter.

The peracid is the reaction product formed by combining:
(i) an organic acid having one to eight carbon atoms;
(ii) an inorganic acid; and
(iii) an inorganic peroxide compound.

A method for controlling microbial populations in the gastrointestinal tract of animals, comprising the step of orally administering an effective amount of a compound having the formula:

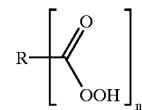

where R is a group selected from alkyl, arylalkyl, cycloalkyl, aromatic or heterocyclic; and where n is one or more.

The peroxide of many organic acids have the attributes of hydrogen peroxide—effective germicidal and sterilizing capabilities, benign decomposition products, and infinite water solubility—but with greater lipid solubility and freedom from deactivation by catalase and peroxidases. The peroxide of acetic acid, peroxyacetic acid, or peracetic acid (PAA) is an effective biocide with no toxic residues and is widely used as a surface disinfectant in the food processing industry. PAA is a more potent antimicrobial agent than hydrogen peroxide alone, being rapidly active at low concentrations against a wide spectrum of microorganisms. It is sporicidal even at low temperatures and remains effective in the presence of organic matter. As a weak acid it is more active on the acid side but is germicidal with higher concentration in the alkaline range. Like hydrogen peroxide (HP), it is useful both in solution and as a vapor. These properties make it a remarkably valuable compound.

Peroxides in general are high-energy-state compounds, and as such can be considered thermodynamically unstable. PAA is considerably less stable than HP. 40% PAA loses 1 to 2% of its active ingredients per month, as compared with HP (30 to 90%), which loses less than 1% per year. The decomposition products of PAA are acetic acid, HP, oxygen, and water. Dilute PAA solutions are even more unstable: a 1% solution loses half its strength through hydrolysis in 6 days.

It may therefore be desirable for the practice of this invention to mix the components of the peracid or peroxygen solution at or near the location at which the biocidal solution is to be used. The individual componets may therefore be prepared commercially as separate containers or matched together such that the number of components for the final formulation is minimized but the stability of the precursor solutions is maximized. PAA is produced by the reaction of acetic acid or acetic anhydride with HP in the presence of sulfuric acid, which acts as a catalyst, as shown:

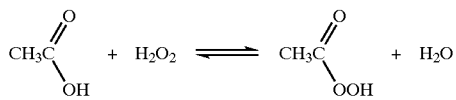

The oxidation of organic carboxylic acids with hydrogen peroxide and an inorganic acid catalyst is the best general method for the preparation of peroxy acids. The most common catalyst for aliphatic R in

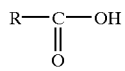

is concentrated sulfuric acid. The reaction is an equilibrium and is driven to the right by removal of water or by the use of excess reagents. For aromatic R the best catalyst is methanesulfonic acid, which can be also used as the solvent.

Peroxygenated carboxylic acids have been shown to have excellent antimicrobial activity and have found utility in disinfecting diverse surfaces. These peroxy carboxylic acids are only moderately stable in aqueous solutions and therefore are most effective when used soon after the solutions are made. Examples of peroxygenated carboxylic acids include the following: performic, peracetic, perproprionic, peroxyheptanoic, peroxynonanoic, perlauric, monoperglutaric, diperglutaric, succinylperoxide, derivatives of perbenzoic acid, magnesium salt of peroxyphthalate, benzoyl peroxide, t-butylhydroperoxide, perlactic, percitric, perbutyric, peroctanoic, and perglycolic. Peroxygenated carboxylic acids are often known as, or referred to, by peracid compounds, peroxygen compounds, peroxo compounds and peroxides of organic acids.

Among other constituents, the invention comprises a carboxylic acid. Generally, carboxylic acids have the formula R—COOH wherein the R may represent any number of different groups including aliphatic groups, alicyclic groups, aromatic groups, heterocyclic groups, all of which may be saturated or unsaturated as well as substituted or unsubstituted. Carboxylic acids also occur having one, two, three, or more carboxylic groups.

Carboxylic acids have a tendency to acidify aqueous compositions in which they are present as the hydrogen atom of the carboxyl group is active. Therefore, the carboxylic acids may appear as an anion in solution. The carboxylic acid constituent within the present composition when combined with aqueous hydrogen peroxide generally functions as an antimicrobial agent as a result of the presence of the active hydrogen atom. Moreover, the carboxylic acid constituent within the invention maintains the composition at an acidic pH.

Carboxylic acids which are generally useful in the process of the invention are those which comprise percarboxylic acids. Percarboxylic acids generally have the formula $R(CO_3H)_n$, where R is an alkyl, arylalkyl, cycloalkyl, aromatic or heterocyclic group, and n is one, two, or three, and named by prefixing the parent acid with peroxy.

Peracid powder disinfectants also useful in this invention can be derived from water plus mixtures of organic acid reservoirs (e.g., anhydrides, amides, and esters) added to hydrogen peroxide reservoirs (e.g., sodium peroxide).

While peroxy carboxylic acids are not very stable, their stability generally increases with increasing molecular weight. Thermal decomposition of these acids may generally proceed by free radical and nonradical paths, by photodecomposition or radical-induced decomposition, or by the action of metal ions or complexes. Percarboxylic acids may be made by the direct, acid catalyzed equilibrium action of 30–98 wt. % hydrogen peroxide with the carboxylic acid, by autoxidation of aldehydes, or from acid chlorides, and hydrides, or carboxylic anhydrides with hydrogen or sodium peroxide.

Percarboxylic acids useful in this invention include peracetic acid, perpropionic acid, perbutyric acid, peroctanoic acid, perglycolic acid, perglutaric acid, persuccinic acid, perlactic acid, percitric acid, perdecanoic acid or mixtures thereof. These percarboxylic acids have been found to provide good antimicrobial action with good stability in aqueous streams.

In addition to peracetic, peroctanoic and perdecanoic, particularly preferred percarboxylic acids include perpropionic, perbutyric, perglycolic, perlactic and percitric acids.

The process of the invention also uses a combination of peracetic acid with other percarboxylic acids, preferably, those named above and particularly, peroctanoic acid. This combination of percarboxylic acids has been found to provide preferred antimicrobial efficacy and stability in the presence of high organic loads. Generally, within the sanitizer, the concentration of, for example, peroctanoic acid may range from about 10 wt-% to 90 wt-% and preferably from about 10 wt-% to 20 wt-%. The concentration of peracetic acid may range from about 10 wt-% 90 wt-% and preferably from about 80 wt-% to 90 wt-%.

The process of the invention also uses peracetic acid. Peracetic acid is a peroxy carboxylic acid having the formula, $CH_3COOOH$. Generally, peracetic acid is a liquid having an acrid odor at high concentrations and is freely soluble in water, alcohol, ether, and sulfuric acid. Peracetic acid may be prepared through any number of means known to those of skill in the art including preparation from acetaldehyde and oxygen in the presence of cobalt acetate. A 50% solution of peracetic acid may be obtained by combining acetic anhydride, hydrogen peroxide and sulfuric acid. Other methods of formulation of peracetic acid include those disclosed in U.S. Pat. No. 2,833,813, which is incorporated herein by reference.

In its most preferred embodiment, the process of the invention uses perlactic acid, $CH_3CH(OH)COOOH$.

Generation of the peroxy acids may be accomplished in various manners known in the art. Specifically, the peroxy acids may be formed through the use of peroxy acid concentrate compositions. In such a case, the percarboxylic acid may either be generated naturally or through the combination of a hydrogen peroxide concentrate together with a carboxylic acid concentrate at the site of use such as that process which is disclosed in Lokkesmoe et al, U.S. Pat. No. 5,122,538, which is incorporated herein by reference. Furthermore, the peroxy acids may be formed by the methods disclosed in Lokkesmoe et al., U.S. Pat. No. 5,674,538, which is incorporated herein by reference.

Hydrogen Peroxide

The antimicrobial composition of the invention may also comprise a hydrogen peroxide constituent. Hydrogen peroxide in combination with the percarboxylic acid provides a surprising level of antimicrobial action against microorganisms despite the presence of skin, tissue and intestinal contents, mucose materials and membrane materials and sediment. Additionally, hydrogen peroxide may provide an effervescent action which may irrigate any surface to which it is applied. An additional advantage of hydrogen peroxide is that combinations of perlactic acid and hydrogen peroxide result in lactic acid, water, and oxygen upon decomposition all of which are food product compatible.

Generally, the concentration of hydrogen peroxide within the composition used in the process of the invention ranges from about 1 weight percent to about 50 weight percent, preferably from about 3 weight percent to about 40 weight percent, and most preferably from about 5 weight percent to about 30 weight percent. This concentration of hydrogen peroxide is most preferred as providing an optimal antimicrobial effect. These concentrations of hydrogen peroxide may be increased or decreased while still remaining within the scope of the invention.

Additives

The antimicrobial composition of the invention may also comprise any number of additives e.g. stabilizing agents, wetting agents, as well as growth factors, growth stimulants, vitamins, mineral supplements, antibiotics, drugs, and other nutrients that aid the growth and health of the animal receiving the formulation.

Stabilizing agents may be added to the composition of the invention to stabilize the percarboxylic and hydrogen peroxide formulation and prevent the premature oxidation of this constituent within the composition of the invention. Chelating agents or sequestrants generally useful as stabilizing agents include: alkyl diamine polyacetic acid-type chelating agents such as EDTA (ethylene diamine tetraacetate tetrasodium salt), acrylic and polyacrylic acid-type stabilizing agents, phosphonic acid, phosphonate-type chelating agents among others.

Preferable sequestrants include: phosphonic acids phosphonate salts including 1-hydroxy ethyldene-1, 1-diphosphonic acid ($CH_3C(PO_3H_2)_2OH$), amino[tri (methylene phosphonic acid)] ($[CH_2PO_3H_2]_2$ (ethylene diamine[tetra methylene-phosphonic acid), 2-phosphene butane-1,2,4-tricarboxylic acid, as well as the alkyl metal salts, ammonium salts, or alkyloyl amine salts, such as mono, di, tri, or tetra-ethanolamine salts. The stabilizing agent is used in a concentration ranging from about 0 weight percent to about 20 weight percent of the composition, preferably from about 0.1 weight percent to about 10 weight percent of the composition, and most preferably from about 0.2 weight percent to 5 weight percent of the composition.

Also useful in the composition of the invention are wetting and defoaming agents. Wetting agents function to increase the penetration activity of the antimicrobial composition of the invention. Wetting agents which may be used in the composition of the invention include any of those constituents known within the art to raise the surface activity of the composition of the invention.

Along these lines surfactants, and especially nonionic surfactants, may also be useful in the present invention. Nonionic surfactants which may be useful in the present invention are those which comprise ethylene oxide moieties, propylene oxide moieties, as well a mixtures thereof, and ethylene oxide-propylene oxide moieties in either heteric or block formation. Additionally useful in the present invention are nonionic surfactants which comprise alkyl ethylene oxide compounds, alkyl propylene oxide compounds, as well as mixtures thereof, and alkyl ethylene oxide-propylene oxide compounds where the ethylene oxide-propylene oxide moiety is either in heteric or block formation. Further useful in the present invention are nonionic surfactants having any mixture or combination of ethylene oxide-propylene oxide moieties linked to a alkyl chain where the ethylene oxide and propylene oxide moieties may be in any randomized or ordered pattern and of any specific length. Nonionic surfactants useful in the present invention may also comprise randomized sections of block and heteric ethylene oxide propylene oxide, or ethylene oxide-propylene oxide.

Generally, the concentration of nonionic surfactant used in the invention may range from about 0 wt-% to about 5 wt-% of the composition, preferably from about 0 wt-% to about 2 wt-% of the concentrate composition, and most preferably from about 0 wt-% to about 1 wt-% of the composition.

The composition used in the process of the invention may also contain additional ingredients as necessary to assist in defoaming.

Generally, defoamers which may be used in accordance with the invention include silica and silicones; aliphatic acids or esters; alcohols; sulfates or sulfonates; amines or amides; halogenated compounds such as fluorochlorohydrocarbons; vegetable oils, waxes, mineral oils as well as their sulfated derivatives; fatty acid soaps such as alkali, alkaline earth metal soaps; and phosphates and phosphate esters such as alkyl and alkaline diphosphates, and tributyl phosphates among others; and mixtures thereof.

Especially preferable, are those antifoaming agents or defoamers which are of food grade quality given the application of the process of the invention. To this end, one of the more effective antifoaming agents comprises silicones. Silicones such as dimethyl silicone, glycol polysiloxane, methylphenol polysiloxane, trialkyl or tetralkyl silanes, hydrophobic silica defoamers and mixtures thereof may all be used in defoaming applications. Commercial defoamers commonly available include silicones such as Ardefoam™ from Armour Industrial Chemical Company which is a silicone bound in an organic emulsion; Foam Kill™ or Kresseo™ available from Krusable Chemical Company which are silicone and non-silicone type defoamers as well as silicone esters; and Anti-Foam™ $^{RTM}$ and DC-200$^{RTM}$ from Dow Corning Corporation which are both food grade type silicones among others. These defoamers are generally present at a concentration range from about 0 wt-% to 5 wt-%, preferably from about 0 wt-% to 2 wt-%, and most preferably from about 0 wt-% to about 1 wt-%.

Food Agents

The formulation can contain flavoring agents, buffering agents and food preservatives: such as ascorbic acid, sorbic acid, citric acid, glutaric acid, phosphoric acid, and malic acid. These additives improve palatability and taste, thereby promoting consumption by the animals. These agents may also improve overall health and nutrition of the animals, as well as promoting further microbial destruction. Mineral salts may also be added. Glucose and sugars may also be added.

Generation of Peroxy Acids

The process of the invention may also be initiated through the use of peroxy acid concentrate compositions. In such a case, the percarboxylic acid may either be generated naturally or through the combination of a hydrogen peroxide concentrate together with a carboxylic acid concentrate at the site of use such as that process which is disclosed in Lokkesmoe et al, U.S. Pat. No. 5,122,538, issued Jun. 16, 1992, which is incorporated herein by reference.

Competitive Exclusion

The application of microorganisms as competitive exclusion microflora for the reduction of pathogen colonization in poultry has been discovered. Competitive exclusion microorganisms including Clostridium spp., *Streptococcus faecalis*, Bifidobacterium spp., and *Bacteroides hypermegas* have been examined. Furthermore, preparations containing several strains of single species, such as Bacteroides spp., Bifidobacterium spp., and Escherichia spp. have also been evaluated. Competitive exclusion diminish the populations of gram-negative enteropathogenic bacteria such as Campylobacter and Salmonella.

The method of this invention can also be applied in tandem with the addition of competitive exclusion microorganisms to the animal. The peroxygen formulation is added to destroy target pathogens, e.g., human enteropathogenic bacteria capable of colonizing poultry. Of particular interest are Salmonella and Campylobacter species. Competitive exclusion microorganisms can be introduced to the intestinal tract subsequently, allowing sufficient time for the active disinfection ingredients to dissipate. The intestines, now harboring reduced numbers of microbial pathogens are more capable of being colonized by the exclusion organisms.

Both peroxygen compounds and competitive exclusion microorganisms can be administered by oral gavage, in drinking water, in feed/foodstuffs, by spraying newly hatched chicks with an aqueous suspension, or a combination of the above. This combined treatment would preferably be performed early and as frequently as possible.

EXAMPLES

The formulations are applied before the slaughter and degutting and cleaning of poultry. The treatment formulations are placed in the drinking water, feed/foodstuffs or litter. However, dual use applications can be applied. This is where intestinal tract disinfection is performed on the live animal in the period before slaughter, such as the feed withdrawal period. The formulations of carboxylic acids are then applied to the meat during gutting, processing cleansing and packaging stages.

Based on in vitro and in vivo data, it appears that the incorporation of freshly made peroxygenated and/or oxygen activated solutions into animal drinking water prior to slaughter may represent an effective approach for the reduction of pathogenic bacteria in the GI tract of food animals. Although Salmonella were the only species studied, it is anticipated that this approach would also be successful for incativating diverse pathogens on a variety of surfaces, including, but not limited to, Campylobacter, *E. coli*, Listeria, other bacteria, viruses, spores, prions, and yet undescribed infectious agents.

Example 1

A variety of chemicals have been evaluated for efficacy as a drinking water-based biocide for administration to birds during the period of feed withdrawal. Ozone, a powerful oxidant with excellent bacteriocidal effects in drinking water, was shown to be a very palatable oxidant. It was found, however, that the biocidal effect of this dissolved, short-lived oxidant was minimal in the crops of market-age broilers. This ineffectiveness is thought to be due primarily to the high ozone demand of the ingesta itself, which consumes the majority of the ozone and subsequently prevents delivery of sufficient ozone to the bacteria surfaces.

Example 2

Organic compounds have been evaluated for biocidal efficacy in the upper GI tract of poultry, including D-limonene. This chemical showed excellent results in vitro; that is, the compound was able to achieve excellent bacterial kills in the presence of potentially interfering compounds found in poultry ingesta. However, broilers demonstrated remarkable water refusal when this compound was introduced into the drinking water, even at the lowest biocidal concentrations. Organic acids have also found utility as a drinking water biocide for gut bacteria. As was the case with the D-limonene compound, acetic acid had excellent in vitro antibacterial capability, but elicited a significant water refusal response. The compound which has demonstrated the most promise for diverse antimicrobial applications in the food industry, without undesirable organoleptic characteristics, is lactic acid.

Example 3

Formulations of Peroxy Compounds (Peracids)

Three peracid solutions were made in the laboratory, diluted to concentrations that were palatable to broiler chickens, evaluated for biocidal activity in vitro at the concentrations that showed promise for palatability, and evaluated in broilers for disinfection of *Salmonella enteritidis* in the crop.

Preparation of Peracetic Acid

To a 250 mL Erlenmeyer flask was added 110.6 grams of glacial acetic acid, 89.4 grams of 35% hydrogen peroxide, and 200 $\mu$L of concentrated sulfuric acid. The contents of the flask were mixed thoroughly. This resulted in a peracetic acid concentration of 12.8 percent of a pure peracetic acid concentration.

Preparation of Perlactic Acid

To a 250 mL Erlenmeyer flask was added 135.6 grams of 88% lactic acid, 64.4 grams of 35% hydrogen peroxide, and 200 $\mu$L of concentrated sulfuric acid. The contents of the flask were mixed thoroughly. This resulted in a perlactic acid concentration of 1.4% of peracetic acid on a wt % basis.

Preparation of Percitric Acid

To a 250 mL Erlenmeyer flask was added 30 grams of citric acid, 7.6 grams of 35% hydrogen peroxide, 200 $\mu$L of concentrated sulfuric acid, and 162.4 grams of deionized water. The contents of the flask were mixed thoroughly. This resulted in a percitric acid concentration of 0.8% of peracetic acid on a wt % basis.

These peracid solutions were diluted in water to various wt % concentrations according to the theoretical concentrations of the resultant peracid as expressed as a % of peracetic acid (based on ceric sulfate/sodium thiosulfate titrations). These diluted peracids were evaluated in vitro and in three studies in vivo (market age broiler chickens).

Example 4

Demonstration of Palatability of Peroxy Acids in Poultry

Broiler chickens (6-week old, n=80), housed in a pathogen isolation building, were given free access to food and water for several days. At 8:00 A.M., the water was removed from the pens which housed 20 birds each. At 3:30 P.M., the water was reintroduced to the birds and the feed was removed; five birds were weighed from each group. The four groups of birds were as follows: Control water (no peracid); 0.05% peracetic acid in the drinking water; 0.0125% perlactic acid in the drinking water; and, 0.0125% percitric acid in the drinking water. The birds were weighed after 2 hours of drinking the peracid or control water to indirectly determine water consumption. The results of this study are shown in FIG. 1.

The data suggests that at the concentrations given to the broilers for the two hours after a seven-hour water removal period, percitric acid was the most palatable. Perlactic was less desired by the birds and peracetic acid caused significant water refusal. Although all treatment groups showed less water consumption after addition of peracid to the drinking water, a general acceptance of perlactic and percitric at lower concentrations is implied.

Example 5

In vitro and in vivo Disinfection of *Salmonella enteritidis*

Figure 2:
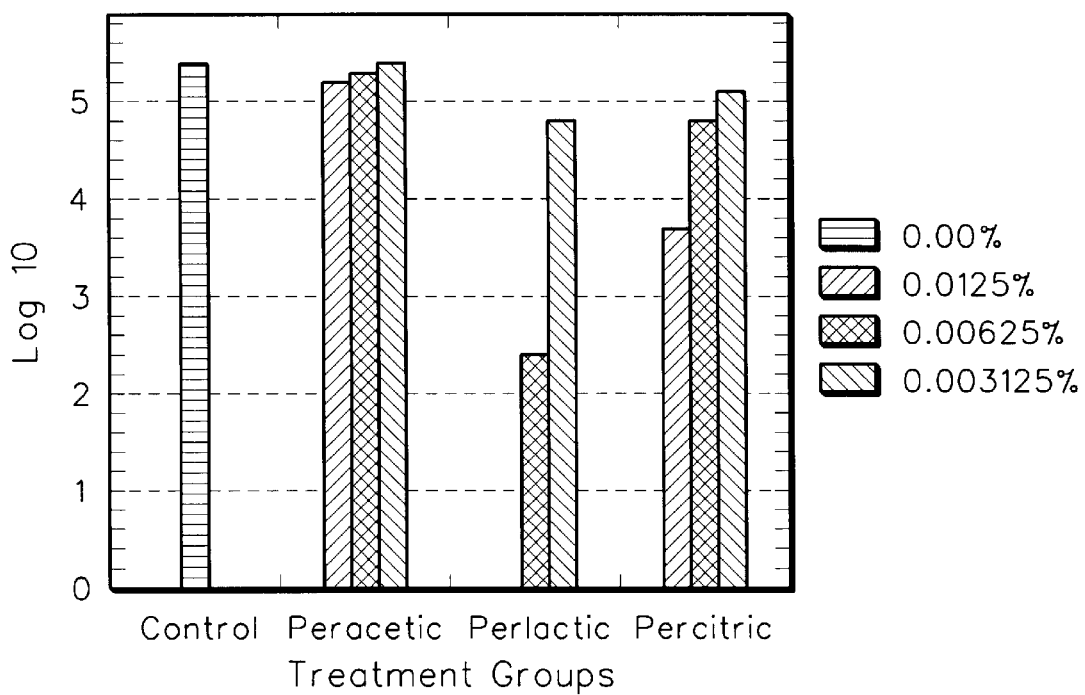
FIG. 2 is a graphical depiction of the in vitro reduction in *Salmonella enteritidis* after exposure to various concentrations of peracetic (PA), perlactic (PL), and percitric acids (PC) in the presence of autoclaved broiler feed.

Another study was performed to determine the bactericidal effects of the same three peracids investigated in the first study. Eleven tubes were filled with 0.5 g of autoclaved broiler feed to which 100 ul of a *Salmonella enteritidis* culture broth was added. Two of the tubes were additionally filled with 1.9 ml of distilled water and the remaining nine were filled with an additional 1.7 ml of $H_2O$. The peracids were added to the nine tubes to achieve a 0.0125% of each of the three peracids and two subsequent dilutions to achieve 0.00625% and 0.003125% of each. The samples were incubated at 37° C. and vortexed. After 1 h, the samples were plated and diluted to yield a plate count of $10^4$ and $10^3$ cfu/ml The results shown in FIG. 2 show that peracetic acid is a poor biocide (at all concentrations) in the presence of the same organic matter which is expected to fill the lumen of upper GI tract of birds during feed withdrawal. Percitric acid showed significant biocidal effects for Salmonella at the highest concentration, but the diluted samples were not as efficient. However, perlactic acid showed a disinfection efficacy at all concentrations. The highest concentration tested eliminated the Salmonella to levels that fell below the detection limit of this assay. These data show that while peracetic acid solutions may not be suitable for a drinking water biocide, perlactic and percitric acids are still good candidates for evaluation in live broilers.

Example 6

To determine the biocidal effect of perlactic and percitric on Salmonella in the upper GI tract (crops) of broiler chickens, peracid solutions were added to the drinkers such that the concentration of perlactic was 0.006 or 0.003% and percitric was at a 0.03% concentration. The birds were deprived of water for 8 h prior to an 8 h feed withdrawal period and allowed to drink the water for 8 h. Prior to reintroduction of the water with the test compounds, the birds were gavaged with 1 ml of $10^8$ Salmonella. After the 8 h test consumption, the birds were terminated, the crops removed aseptically, stomached for 30 seconds, diluted and plated onto BGA with NO/NA.

Figure 3:
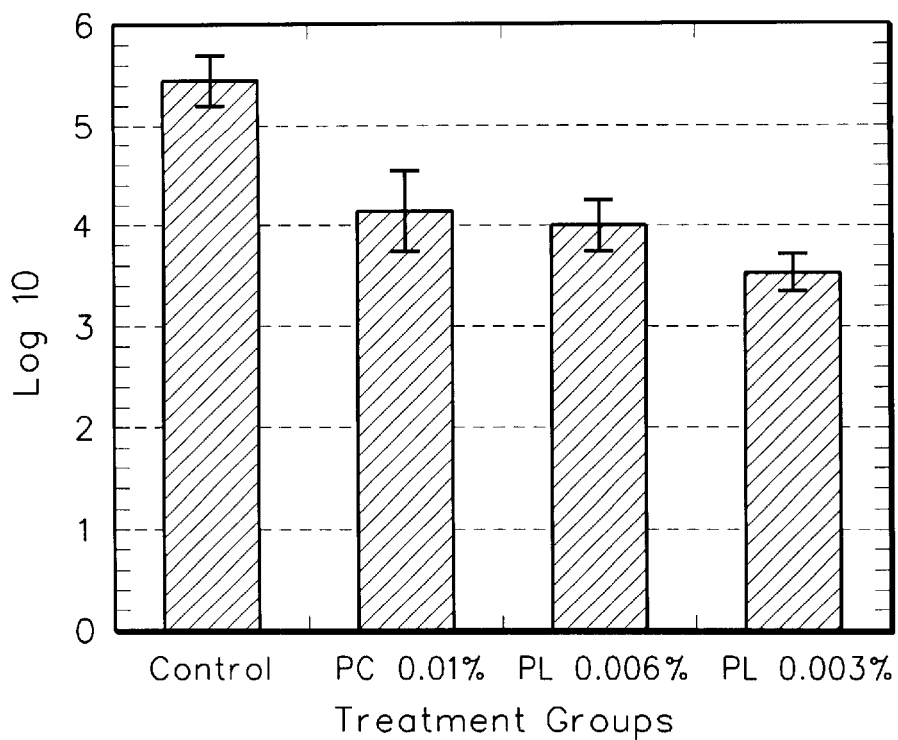
FIG. 3 is a graphical depiction of the reduction of *Salmonella enteritidis* in broiler crops after exposure to percitric (PC), perlactic (PL), or peracetic acid (PA) in the drinking water during 8 h of feed withdrawal.

The results shown in FIG. 3 demonstrate, for the first time, that perlactic and percitric acids are effective in achieving a multiple log reduction of Salmonella in the crop after only 8 h of exposure to the drinking water chemical. It also appears that perlactic can achieve a greater bactericidal effect at lower concentrations than percitric, making it the best candidate for further studies. Further, the two log reduction of Salmonella at 0.003%, coupled with the in vitro and palatability data, suggests that higher concentrations of lactic may also be used to achieve even greater kills in the GI tract.

Example 7

Another experiment was designed to further characterize the disinfection effect of perlactic acids when different consumption pressures were placed on 8 week-old broilers. All of the birds had the feed removed 8 hours prior to slaughter. Perlactic acid was added at 0.003125% (30 ppm) to the drinking water for the last 8 hours of the study (feed withdrawal period). The first treatment group had water removed 8 hours prior to the 8 h feed withdrawal (PL 8-8-8) and the second treatment group had only feed withdrawal/perlactic treatment (PL 8—8). The last group had access to the peracid in their drinking water 12 hours prior to slaughter and the feed taken up 4 hours after that yielding a final feed withdrawal time of 8 h (PL 12-8). At the conclusion of the study, the crops were processed microbiologically similar to the methods described for FIG. 3.

Figure 4:
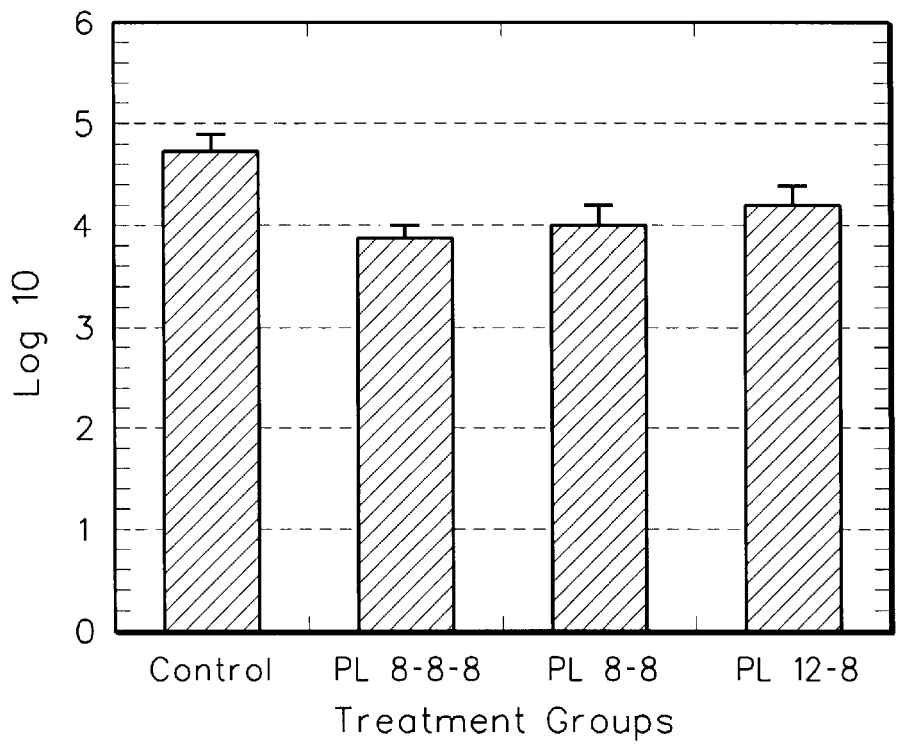
FIG. 4 is a graphical depiction of the reduction of *Salmonella enteritidis* in broiler crops after exposure to 0.003% perlactic acid solution in drinking water during feed withdrawal, both with and without 8 h water restriction.

The results in FIG. 4 show that increased biocide exposure time or water deprivation prior to feed withdrawal does not increase the biocidal effect of the perlactic solutions. Additionally, the results obtained in this study suggest that the effectiveness of the perlactic solutions was diminished when compared to the results obtained in FIG. 3. The reason for this is not clear; however, these two studies were performed 1 week apart but used the same perlactic concentrate, suggesting that the biocidal component(s) of the perlactic solution had degraded over time. This is in agreement with the literature which has shown that peracid formulations are unstable and will degrade over a period of several days. Therefore, it is believed that an effective drinking water peracid delivery device would have to be capable of metering and mixing the peracid solutions fresh as they are needed in the drinker devices at the animal feeding facility.

Example 8

In the final broiler study, forty-five 8-week old broilers were divided up into 3 groups with 13/group. Upon feed withdrawal, all birds were gavaged with 1 ml of a $1\times10^8$ challenge of *Salmonella enteritidis*. At this time, all feed was removed and the drinking water treatments administered. Group 1 (control) received only water, group 2 (PL 30 ppm) received perlactic acid with the substrate added and group 3 (L+$H_2O_2$ 30 ppm) received a combination of lactic acid and hydrogen peroxide, without the addition of the inorganic acid catalyst component, at the same concentrations as the perlactic acid. All groups received the same withdrawal time of 8 hours. At the time of kill, the crops were aseptically collected after cervical dislocation. The crops were added to whirl-pac bags containing 10 ml of PBS. The bags were stomached for 30 sec where upon 250 µl were removed and added to 2.25 ml of PBS. After stomaching, 0.5 ml was removed and added to 4.5 ml PBS for dilution purposes; 100 µl per tube were then plated onto BGA with NO/NA. Groups 2 and 3 were directly plated from the whirl-pac bags by taking 100 µl from the bag and spread plating it onto BGA plates. These plates were incubated for 24 hrs at 37° C. The plates were counted for CFUs and log 10 reductions. After the bags had been used for dilution purposes, 9.0 ml of tetrathionate broth was added for enrichment purposes. These bags were incubated along with the plates. 24 hours later, 1 loopful of the bag contents were streaked onto BGA plates for +/− observations.

Figure 5:
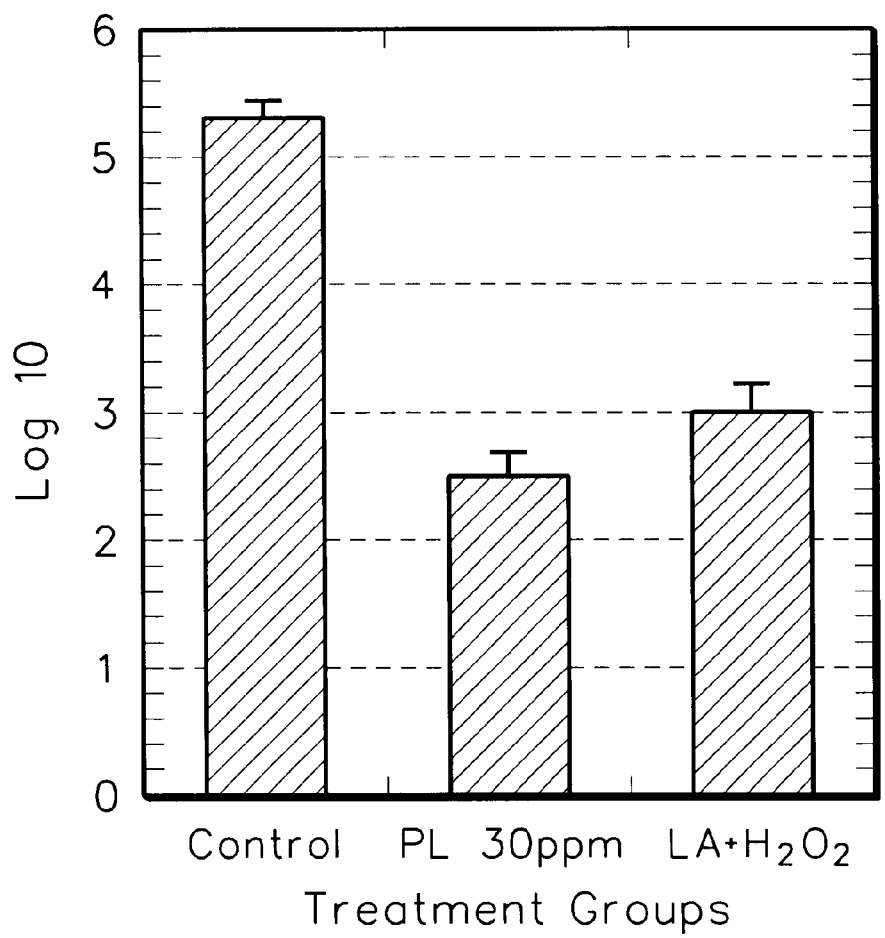
FIG. 5. Graphical depiction of the reduction of Salmonella in broilers consuming water (control), 30 ppm perlactic acid (PL) solution, and the two main parent constituents of the perlactic acid solution, lactic acid (LA) and hydrogen peroxide ($H_2O_2$) together.

Perlactic acid at 30 ppm (group 2) and lactic acid and hydrogen peroxide (group 3) were applied to the drinking water of SE challenged broilers as treatment groups. The control group received water alone. Perlactic acid (group 2) applied to the drinking water for 8 hours achieved a 2.71 Log10 reduction in Salmonella in the crop while lactic acid with hydrogen peroxide without the addition of inorganic acid (group3) applied to the drinking water for 8 hours had only a 2.23 Log10 reduction as compared to the control (FIG. 5.). While the difference between the two treatment groups shows only a half log difference in biocidal effectiveness, this data suggests that the preformed peracid solutions have a greater biocidal potential than the peroxide and acid alone.

Example 9

Sporicidal Activity of Peroxy Acids

An experiment was performed to assess at what concentration peroxygen compounds should be incorporated into a decontamination gel formulation for disinfection of surfaces. Since peroxygen compounds, particularly peracetic acid, have limited stability, it is preferable that the hydrogen peroxide and the acetic acid are mixed at or close to the time of use. Glass slides, on which were heat-fixed *Bacillus subtilis* spores, were dipped into the treatment solution for 15 minutes. The slides were then removed from the treatment solution and vigorously flushed with water to remove any residual biocide (either acid, peracid, or peroxide). The spores were removed from the glass slide by sonicating in PBS (buffer) for one hour. Dilutions were plated to determine how many colony-forming units (CFU) were present per milliliter.

The results from these experiments are listed in Table 1. The table describes some experiments that were done to determine the effects of acetic acid concentration, hydrogen peroxide concentration, and the presence or absence of gel (fumed silica) on the destruction of Bacillus subtilis spores. The concentration of acetic acid (HOAc) was mixed with an equal volume of the concentration of hydrogen peroxide ($H_2O_2$) and used to treat spore coated glass slides.

It is apparent from Formulation #1 that mixing equal volumes of 12 M acetic acid with 2.2 M hydrogen peroxide produces a very potent sporicidal agent. Likewise, more dilute mixtures (Formations #2 and #3) are also very effective. This sporicidal effect is independent of the gel because identical results are obtained when the gel is omitted (Formulation #4). The comparison of the sporicidal effect of Formulations #4, #5, and #6, demonstrate that the mixture of hydrogen peroxide and acetic acid is considerably better than either solution by itself and is also better than the sum of the effects of the acetic acid and peroxide solutions. This result implies the formation of peracetic acid.

TABLE 1

Treatment of Bacillus subtilis spores with peracetic acid formulations

| Formulation | Presence of Fumed Silica | [HOAc] (M)[a] | [$H_2O_2$] (M) | HOAc:$H_2O_2$ Ratio | Spore log reduction |
|---|---|---|---|---|---|
| 1 | Yes | 12 | 2.2 | 5.5 | >7.5 |
| 2 | Yes | 5.0 | 0.90 | 5.6 | >7.5 |
| 3 | Yes | 1.2 | 0.22 | 5.5 | >7.5 |
| 4 | No | 12 | 2.2 | 5.5 | >7.5 |
| 5 | No | 12 | 0 | NA | 4.4 |
| 6 | No | 12 | 2.2 | 0 | 1.9 |

[a]Catalytic amounts of sulfuric acid were included in the acetic acid solution to increase the rate of peracid formation.

What is claimed is:

1. A biocide for ingestion by live animals, comprising:
   an organic acid having one to eight carbon atoms;
   an inorganic peroxide compound; and
   at least one agent selected from wetting agents, stabilizing agents, defoaming agents, and combinations thereof.

2. The biocide of claim 1, wherein the inorganic peroxide is selected from hydrogen peroxide, sodium peroxide, potassium peroxide, calcium peroxide, perborates, percarbonates, persulfates, permanganates, and combinations thereof.

3. The biocide of claim 2, wherein the biocide has an inorganic peroxide concentration of between about 1% and about 50%.

4. The biocide of claim 2, wherein the biocide has a hydrogen peroxide concentration of between about 1 wt % and about 50 wt %.

5. The biocide of claim 2, wherein the biocide has a hydrogen peroxide concentration of between about 3 wt % and about 40 wt %.

6. The biocide of claim 2, wherein the biocide has a hydrogen peroxide concentration of between about 5 wt % and about 30 wt %.

7. The biocide of claim 1, wherein the defoaming agents are silicones selected from dimethyl silicones, glycol polysiloxane, methylphenol polysiloxane, trialkyl silanes, tetraalkyl silanes, hydrophobic silica defoamers and combinations thereof.

8. The biocide of claim 7, wherein the biocide has a defoaming agent concentration of between about 0 wt % and about 5 wt %.

9. The biocide of claim 7, wherein the biocide has a defoaming agent concentration of between about 0 wt % and about 2 wt %.

10. The biocide of claim 7, wherein the biocide has a defoaming agent concentration of between about 0 wt % and about 1 wt %.

11. The biocide of claim 1, wherein the defoaming agents are selected from aliphatic acids, aliphatic esters, alcohols, sulfates, sulfonates, amines, amides, halogenated compounds, vegetable oils, waxes, mineral oils, fatty acid soaps, phosphates, phosphate esters, tributyl phosphates, and combinations thereof.

12. The biocide of claim 11, wherein the biocide has a defoaming agent concentration of between about 0 wt % and about 5 wt %.

13. The biocide of claim 11, wherein the biocide has a defoaming agent concentration of between about 0 wt % and about 2 wt %.

14. The biocide of claim 1, wherein the stabilizing agents comprise chelating agents.

15. The biocide of claim 1, wherein the stabilizing agents comprise sequestrants.

16. The biocide of claim 1, wherein the biocide has a stabilizing agent concentration of between about 0 wt % and about 20 wt %.

17. The biocide of claim 1, wherein the biocide has a stabilizing agent concentration of between about 0.1 wt % and about 10 wt %.

18. The biocide of claim 1, wherein the biocide has a stabilizing agent concentration of between about 0.2 wt % and about 5 wt %.

19. The biocide of claim 1, wherein the surfactant is nonionic.

20. The biocide of claim 1, wherein the biocide has a surfactant concentration of between about 0 wt % to about 5 wt %.

21. The biocide of claim 1, wherein the biocide has a surfactant concentration of between about 0 wt % to about 2 wt %.

22. The biocide of claim 1, wherein the biocide has a surfactant concentration of between about 0 wt % to about 1 wt %.

23. The biocide of claim 1, wherein the animals are selected from humans and other vertebrate animals.

24. The biocide of claim 1, wherein the animals are poultry.

25. The biocide of claim 1, wherein the organic acid is a percarboxylic acid.

26. The biocide of claim 1, wherein the organic acid is selected from perlactic acid, percitric acid, peracetic acid and combinations thereof.

27. The biocide of claim 1, wherein the organic acid is selected from lactic acid, citric acid, acetic acid and combinations thereof.

28. The biocide of claim 1, wherein the organic acid is selected from performic, peracetic, perproprionic, peroxyheptanoic, peroxynonanoic, perlauric, monoperglutaric, diperglutaric, succinylperoxide, derivatives of perbenzoic acid, magnesium salt of peroxyphthalate, benzoyl peroxide, t-butylhydroperoxide, perlactic, percitric, perbutyric, peroctanoic, and perglycolic.

29. The biocide of claim 1, wherein the animals ingest the biocide by being administered the biocide orally.

30. The biocide of claim 1, wherein the animals ingest the biocide by drinking the biocide provided in drinking water.

31. The biocide of claim 1, wherein the animals ingest the biocide by eating the biocide provided in feed/foodstuffs.

32. The biocide of claim 1, wherein the animals ingest the biocide over a period just preceding slaughter.

33. The biocide of claim 1, wherein the amount of biocide ingested is effective as a biocide.

34. The biocide of claim 1, wherein the amount of biocide ingested is effective to reduce the population of microbes selected from Salmonella, Campylobacter, E. Coli, Listeria, and Helicobacter.

35. A biocide for ingestion by live animals, comprising:
a peracid compound; and
at least one agent selected from wetting agents, stabilizing agents, defoaming agents, and combinations thereof.

36. The biocide of claim 35, wherein the defoaming agents are silicones selected from dimethyl silicones, glycol polysiloxane, methylphenol polysiloxane, trialkyl silanes, tetraalkyl silanes, hydrophobic silica defoamers and combinations thereof.

37. The biocide of claim 36, wherein the biocide has a defoaming agent concentration of between about 0 wt % and about 5 wt %.

38. The biocide of claim 36, wherein the biocide has a defoaming agent concentration of between about 0 wt % and about 2 wt %.

39. The biocide of claim 36, wherein the biocide has a defoaming agent concentration of between about 0 wt % and about 1 wt %.

40. The biocide of claim 36, wherein the defoaming agents are selected from aliphatic acids, aliphatic esters, alcohols, sulfates, sulfonates, amines, amides, halogenated compounds, vegetable oils, waxes, mineral oils, fatty acid soaps, phosphates, phosphate esters, tributyl phosphates, and combinations thereof.

41. The biocide of claim 40, wherein the biocide has a defoaming agent concentration of between about 0 wt % and about 5 wt %.

42. The biocide of claim 40, wherein the biocide has a defoaming agent concentration of between about 0 wt % and about 2 wt %.

43. The biocide of claim 35, wherein the stabilizing agents comprise chelating agents.

44. The biocide of claim 35, wherein the stabilizing agents comprise sequestrants.

45. The biocide of claim 35, wherein the biocide has a stabilizing agent concentration of between about 0 wt % and about 20 wt %.

46. The biocide of claim 35, wherein the biocide has a stabilizing agent concentration of between about 0.1 wt % and about 10 wt %.

47. The biocide of claim 35, wherein the biocide has a stabilizing agent concentration of between about 0.2 wt % and about 5 wt %.

48. The biocide of claim 35, wherein the surfactant is nonionic.

49. The biocide of claim 35, wherein the biocide has a surfactant concentration of between about 0 wt % to about 5 wt %.

50. The biocide of claim 35, wherein the biocide has a surfactant concentration of between about 0 wt % to about 2 wt %.

51. The biocide of claim 35, wherein the biocide has a surfactant concentration of between about 0 wt % to about 1 wt %.

52. The biocide of claim 35, wherein the animals are selected from humans and other vertebrate animals.

53. The biocide of claim 35, wherein the animals are poultry.

54. The biocide of claim 35, wherein the organic acid is a percarboxylic acid.

55. The biocide of claim 35, wherein the organic acid is selected from perlactic acid, percitric acid, peracetic acid and combinations thereof.

56. The biocide of claim 35, wherein the organic acid is selected from performic, peracetic, perproprionic, peroxyheptanoic, peroxynonanoic, perlauric, monoperglutaric, diperglutaric, succinylperoxide, derivatives of perbenzoic acid, magnesium salt of peroxyphthalate, benzoyl peroxide, t-butylhydroperoxide, perlactic, percitric, perbutyric, peroctanoic, and perglycolic.

57. The biocide of claim 35, wherein the animals ingest the biocide by being administered the biocide orally.

58. The biocide of claim 35, wherein the animals ingest the biocide by drinking the biocide provided in drinking water.

59. The biocide of claim 35, wherein the animals ingest the biocide by eating the biocide provided in feed/foodstuffs.

60. The biocide of claim 35, wherein the animals ingest the biocide over a period just preceding slaughter.

61. The biocide of claim 35, wherein the amount of biocide ingested is effective as a biocide.

62. The biocide of claim 35, wherein the amount of biocide ingested is effective to reduce the population of microbes selected from Salmonella, Campylobacter, E. Coli, Listeria, and Helicobacter.

* * * * *